United States Patent [19]

Nelson

[11] Patent Number: 4,686,245
[45] Date of Patent: Aug. 11, 1987

[54] HIGH ENERGY IRRADIATED POLYCARBONATES CONTAINING ORGANIC BORATES

[75] Inventor: Linda H. Nelson, Evansville, Ind.

[73] Assignee: General Electric Company, Mt. Vernon, Ind.

[21] Appl. No.: 688,372

[22] Filed: Jan. 2, 1985

[51] Int. Cl.$^4$ .............................. C08K 5/55; C08J 3/28
[52] U.S. Cl. .................................... 522/163; 524/183; 524/184; 524/185
[58] Field of Search ........................ 260/462 R, 462 C; 522/163; 524/183, 184, 185; 252/478; 128/303 R, 321, 334 R, 346

[56] References Cited

U.S. PATENT DOCUMENTS

| | | | |
|---|---|---|---|
| 2,942,021 | 6/1960 | Groszos et al. | 524/185 |
| 2,967,877 | 1/1961 | Groszos | 524/184 |
| 3,106,573 | 10/1963 | Bamford | 252/478 |
| 3,156,673 | 11/1964 | Bamford | 252/478 |
| 3,161,606 | 12/1964 | Rash | 252/478 |
| 4,211,679 | 7/1980 | Mark et al. | 524/183 |
| 4,275,174 | 6/1981 | Tadokoro et al. | 252/478 |

FOREIGN PATENT DOCUMENTS 915443  2/1961  United Kingdom .

Primary Examiner—Veronica P. Hoke
Attorney, Agent, or Firm—Martin B. Barancik

[57] ABSTRACT

A composition sufficiently irradiated to achieve sterilization comprising an aromatic carbonate polymer in admixture with an anti-yellowing upon exposure to sterilization irradiation effective amount of a boron compound having part of its structure at least one

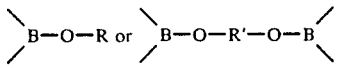

group wherein R is selected from alkyl of one to twenty-four carbon atoms, inclusive, alkenyl of two to twenty-four carbon atoms, inclusive, cycloalkyl of four to fourteen carbon atoms, inclusive, aryl of six to fourteen carbon atoms, inclusive; and substituted phenyl wherein there are one to three substituents which are the same or different and are alkyl of one to six carbon atoms, inclusive, alkoxy of one to six carbon atoms, inclusive, and halo; and R' is selected from the same group as R with a further hydrogen atom replaced by a bond to the second oxygen.

42 Claims, No Drawings

HIGH ENERGY IRRADIATED POLYCARBONATES CONTAINING ORGANIC BORATES

BACKGROUND OF THE INVENTION

Aromatic carbonate polymers are well known thermoplastic materials which, due to their many advantageous properties, find use as thermoplastic engineering materials. The aromatic carbonate polymers exhibit, for example, excellent properties of toughness, impact resistance, heat resistance and dimensional stability. Not only are molded parts prepared from aromatic carbonate polymers, but films and sheet materials as well. Because of its excellent property spectrum, aromatic carbonate polymers such as aromatic polycarbonate have been proposed for various utilities including those relating to medical packaging, for example the containers in which syringes, surgical instruments, intravenous fluids, operating room devices, and the like are maintained. Additionally polycarbonate has been used in medical devices such as blood oxygenators, anesthesia canisters, intravenous connectors and accessories, blood centrifuge bowls, surgical instruments and operating room instruments. The toughness of the polycarbonate as well as its clarity, high heat resistance, strength and good blood compatibility make it a potential substance of choice in this high technology medical device and packaging market. Sterilization of these articles used in the medical arts and other technologies is often times required.

However, one particular difficulty with certain sterilization techniques has been discovered. A typical method of sterilizing various objects useful in medical practice is through irradiation. The type of radiation usually employed is low level gamma radiation. It is readily apparent that the level of gamma radiation which accomplishes the sterilization is significantly above that of ordinary background radiation. When exposed to radiation which is of sufficient strength and duration to sterilize various objects, the aromatic carbonate polymeric material is subject to yellowing. This yellowing changes the color of the aromatic carbonate, thus reducing its utility for this particular application. Not only packaging materials such as flexible aromatic carbonate film and sheet products but also molded parts as well suffer from this 10 yellowing phenomenon.

A new family of additives has been discovered which inhibits the yellowing of aromatic carbonate polymers after exposure to sterilization irradiation. By sterilization irradiation is meant irradiation which kills microorganisms.

DESCRIPTION OF THE INVENTION

In accordance with the invention, there is a composition sufficiently irradiated to achieve sterilization comprising a polycarbonate in admixture with an anti-yellowing upon exposure to sterilization irradiation effective quantity of a boron compound wherein there is at least one

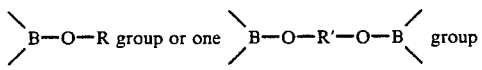

present in the boron compound.

In further accordance with the invention there is a method for reducing yellowing of an irradiated aromatic carbonate polymer which comprises irradiating a composition comprising an aromatic carbonate polymer and an anti-yellowing upon exposure to sterilization irradiation effective quantity of a boron compound wherein there is at least one

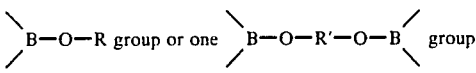

present in the boron compound.

A further aspect of the invention is a composition comprising an aromatic carbonate polymer in admixture with an anti-yellowing upon exposure to sterilization irradiation effective amount of a boron compound of the formula

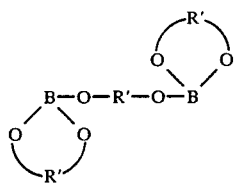

The symbols R and R' are defined further in the specification.

DETAILED DESCRIPTION OF THE INVENTION

Aromatic carbonate polymer generally includes both the polycarbonates and the copolyestercarbonates. The aromatic polycarbonate resins for use herein can be prepared by reacting a dihydric phenol with a carbonate precursor, such as phosgene, a haloformate or a carbonate ester. Generally speaking, such carbonate polymers may be typified as possessing recurring structural units of the formula:

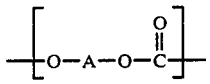

FIG. 1 wherein A is a divalent aromatic radical of the dihydric phenol employed in the polymer producing reaction. Preferably, the carbonate polymers used to provide the resinous mixtures of the invention have an intrinsic viscosity (as measured in methylene chloride at 25° C.) ranging from about 0.30 to about 1.00 dl/g. The dihydric phenols which may be employed to provide such aromatic carbonate polymers are mononuclear or polynuclear aromatic compounds, containing as functional groups two hydroxy radicals, each of which is attached directly to a carbon atom of an aromatic nucleus. Typical dihydric phenols are:
2,2-bis(4-hydroxyphenyl)propane;
hydroquinone;
resorcinol;
2,2-bis-(4-hydroxyphenyl)pentane;
2,4'-dihydroxydiphenylmethane;
bis-(2-hydroxyphenyl)methane;
bis-(4-hydroxyphenyl)methane;
bis-(4-hydroxy-5-nitrophenyl)methane;

1,1-bis(4-hydroxyphenyl)ethane;
3,3-bis(4-hydroxyphenyl)pentane;
2,2-dihydroxydiphenyl;
2,6-dihydroxynaphthalene;
bis-(4-hydroxydiphenyl)sulfone;
bis-(3,5-diethyl-4-hydroxyphenyl)sulfone;
2,2-bis-(3,5-dimethyl-4-hydroxyphenyl)propane;
2,4'-dihydroxydiphenyl sulfone;
5'-chloro-2,4'-dihydroxydiphenyl sulfone;
bis-(4-hydroxyphenyl)diphenyl sulfone;
4,4'-dihydroxydiphenyl ether;
4,4'-dihydroxy-3,3'-dichlorodiphenyl ether;
4,4'-dihydroxy-2,5-dihydroxydiphenyl ether; and the like.

Other dihydric phenols which are also suitable for use in the pre the above polycarbonates are disclosed in U.S. Pat. Nos. 2,999,835; 3,028,365; 3,334,154; and 4,131,575.

These aromatic polycarbonates can be manufactured by known processes, such as, for example and as mentioned above, by reacting a dihydric phenol with a carbonate precursor, such as phosgene, in accordance with methods set forth in the above-cited literature and U.S. Pat. Nos. 4,018,750 and 4,123,436, or by transesterification processes such as are disclosed in U.S. Pat. No. 3,153,008, as well as other processes known to those skilled in the art.

It is possible to employ two or more different dihydric phenols or a copolymer of a dihydric phenol with a glycol or with a hydroxy or acid terminated polyester or with a dibasic acid in the event a carbonate copolymer or interpolymer rather than a homopolymer is desired for use in the preparation of the polycarbonate mixtures of the invention. Branched polycarbonates are also useful, such as are described in U.S. Pat. No. 4,001,184, also there can be utilized blends of a linear polycarbonate and a branched polycarbonate. Moreover, blends of any of the above materials may be employed in the practice of this invention to provide the aromatic polycarbonate. In any event, the preferred aromatic carbonate polymer for use as component (a) (i) herein is a homopolymer derived from 2,2-bis(4-hydroxyphenyl)propane (bisphenol-A).

The copolyestercarbonate usually employed may generally be described as polymers comprising recurring carbonate groups,

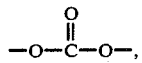

carboxylate groups,

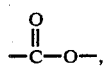

and aromatic carbocyclic groups in the linear polymer chain, in which at least some of the carboxylate groups and at least some of the carbonate groups are bonded directly to ring carbon atoms of the aromatic carboxylic groups. These copolyestercarbonate copolymers in general, are prepared by reacting a difunctional carboxylic acid or ester forming derivative, a dihydric phenol and a carbonate precursor.

The dihydric phenols useful in formulating the copolyestercarbonates for use herein may be represented by the general formula:

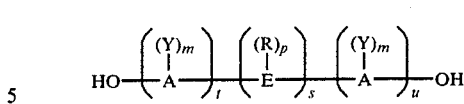

FIG. II.

in which A is an aromatic group such as phenylene, biphenylene, naphthylene, anthrylene, etc. E may be an alkylene or alkylidene group such as methylene, ethylene, propylene, propylidene, isopropylidene, butylene, butylidene, isobutylidene, amylene, isoamylene, amylidene, isoamylidine and generally from one to twelve carbon atoms, inclusive, etc. Where E is an alkylene or alkylidene group, it may also consist of two or more alkylene or alkylidene groups, connected by a nonalkylene or non-alkylidene group such as an aromatic linkage, a tertiary amino linkage, an ether linkage, a carbonyl linkage, a silicon-containing linkage, or by a sulfur-containing linkage such as sulfide, sulfoxide, sulfone, etc. In addition, E may be a cycloaliphatic group of five to seven carbon atoms, inclusive (e.g. cyclopentyl, cyclohexyl), or a cycloalkylidene of five to seven carbon atoms inclusive, such as cyclohexylidene, a sulfur containing linkage, such as sulfide, sulfoxide or sulfone; an ether linkage; a carbonyl group; a tertiary nitrogen group, or a silicon containing linkage such as silane or siloxy. Other groups which E may represent will occur to those skilled in the art. R is hydrogen or a monovalent hydrocarbon group such as alkyl of one to eight carbon atoms, inclusive (methyl, ethyl, propyl, etc.), aryl (phenyl, naphthyl, etc.), aralkyl (benzyl, ethylpehnyl, etc.) or cycloaliphatic of five to seven carbon atoms, inclusive (cyclopentyl, cyclohexyl, etc.). Y may be an inorganic atom such as chlorine, bromine, fluorine, etc.; an organic group such as the nitro group, etc.; an organic group such as R above, or an oxy group such as OR, it being only necessary that Y be inert to and unaffected by the reactants and the reaction conditions. The letter m is any whole number from and including zero through the number of positions on A available for substitution; p is any whole number from and including zero through the number of available positions on E; t is a whole number equal to at least one, S is either zero or one, and u is any whole number including zero.

In the dihydric phenol compound represented by Formula II above, when more than one Y substituent is present, they may be the same or different. The same is true for the R substituent. Where s is zero in Formula II and u is not zero, the aromatic rings are directly joined with no intervening alkylene or other bridge. The positions of the hydroxyl groups and Y on the aromatic nuclear residues A can be varied in the ortho, meta, or para positions and the groupings can be in a vicinal, asymmetrical or symmetrical relationship, where two or more ring carbon atoms of the aromatic hydrocarbon residue are substituted with Y and hydroxyl group.

Examples of dihydric phenol compounds that may be employed in the copolyestercarbonate include:
2,2-bis-(4-hydroxyphenyl)propane (bisphenol-A);
2,4'-dihydroxydiphenylmethane;
bis-(2-hydroxyphenyl)methane;
bis-(4-hydroxyphenyl)methane;
bis-(4-hydroxy-5-nitrophenyl)methane;
bis-(4-hydroxy-2,6-dimethyl-3-methoxyphenyl methane
1,1-bis-(4-hydroxyphenyl)ethane;
1,2-bis-(4-hydroxyphenyl)ethane;
1,1-bis-(4-hydroxy-2-chlorophenyl)ethane;

1,1-bis-(2,5-dimethyl-4-hydroxyphenyl)ethane;
1,3-bis-(3-methyl-4-hydroxyphenyl)propane;
2,2-bis-(3-phenyl-4-hydroxyphenyl)propane;
2,2-bis-(3-isopropyl-4-hydroxyphenyl)propane;
2,2-bis-(4-hydroxynaphthyl)propane;
2,2-bis-(4-hydroxyphenyl)pentane;
3,3-bis-(4-hydroxyphenyl)pentane;
2,2-bis-(4-hydroxyphenyl)heptane;
bis-(4-hydroxyphenyl)phenylmethane;
bis-(4-hydroxyphenyl)cyclohexylmethane;
1,2-bis-(4-hydroxyphenyl)-1,2-bis-(phenyl)propane;
2,2-bis-(4-hydroxyphenyl)-1-phenylpropane; and the like.

Also included are dihydroxybenzenes typified by hydroquinone and resorcinol, dihydroxydiphenyls such as 4,4'-dihydroxydiphenyl; 2,2'-dihydroxydiphenyl; 2,4'-dihydroxydiphenyl; dihydroxy-naphthalenes such as 2,6-dihydroxynaphthalene, etc.

Also useful are dihydric phenols wherein E is a sulfur containing radical such as the dihydroxy aryl sulfones exemplified by: bis-(4-hydroxyphenyl)sulfone; 2,4'-dihydroxydiphenyl sulfone; 5-chloro-2,4'-dihydroxy diphenyl sulfone; 3-chloro-bis-(4hydroxyphenyl)sulfone; and 4,4'-dihydroxytriphenyldisulfone; etc. The preparation of these and other useful sulfones are described in U.S. Pat. No. 2,288,282. Polysulfones as well as substituted sulfones using halogen, nitrogen, alkyl radicals, etc. are also useful.

Dihydroxy, aromatic ethers such as those described in U.S. Pat. No. 3,148,172 are useful as the dihydric phenol herein. The dihydroxy aromatic ethers may be prepared as described in U.S. Pat. No. 2,739,171. Illustrative of such compounds are the following:
4,4'-dihydroxydiphenyl ether;
4,4'-dihydroxytriphenyl ether;
the 4,3'-, 4,2'-, 4,1'-, 2,2'-, 2,3'-, etc. dihydroxydiphenyl ethers;
4,4'-dihydroxy-2,6-dimethyldiphenyl ether;
4,4'-dihydroxy-2,5-dimethyldiphenyl ether;
4,4'-dihydroxy-3,3'-diisobutyldiphenyl ether;
4,4'-dihydroxy-3,3'-diisopropyldiphenyl ether;
4,4'-dihydroxy-3,3'-dinitrodiphenyl ether;
4,4'-dihydroxy-3,3'-dichlorodiphenyl ether;
4,4'-dihydroxy-3,3'-difluorodiphenyl ether;
4,4'-dihydroxy-2,3'-dibromodiphenyl ether;
4,4'-dihydroxydinaphthyl ether;
4,4'-dihydroxy-3,3'-dichlorodinaphthyl ether;
2,4-dihydroxytetraphenyl ether;
4,4'-dihydroxypentaphenyl ether;
4,4'-dihydroxy-2,6-dimethoxydiphenyl ether;
4,4'-dihydroxy-2,5-diethoxy-diphenyl ether, etc.

Mixtures of the dihydric phenols can also be employed and where dihydric phenol is mentioned herein, mixtures of such materials are considered to be included.

In general, any difunctional carboxylic acid or its reactive derivative such as the acid halide conventionally used in the preparation of polyesters may be used for the preparation of polyestercarbonates useful in formulating the compositions of the present invention. In general, the carboxylic acids which may be used include the aliphatic carboxylic acids, aliphatic aromatic carboxylic acids, or aromatic carboxylic acids. The aromatic dicarboxylic acids or their reactive derivatives such as the aromatic diacid halides are preferred as they produce the aromatic polyestercarbonates which are most useful, from the standpoint of physical properties, in the practice of the instant invention.

These carboxylic acids may be represented by the general formula:

$$R^2\text{--}(R^1)_q\text{COOH} \qquad \text{FIG. III.}$$

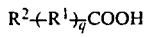

wherein $R^1$ represents an alkylene, alkylidene or cycloaliphatic group in the same manner as set out above for E in Formula II; an alkylene, alkylidene or cycloaliphatic group containing ethylenic unsaturation; an aromatic radical such as phenylene, naphthylene, bisphenylene, substituted phenylene, etc.; two or more aromatic groups connected through non-aromatic linkages such as those defined by E in Formula II; or a divalent aliphatic aromatic hydrocarbon radical such as an aralkyl or alkaryl radical. $R^2$ is either a carboxyl or a hydroxyl group. The letter q represents the integer one where $R^2$ is a hydroxyl group and either zero or one where $R^2$ is a carboxyl group. Thus the difunctional carboxylic acid will either be a monohydroxy monocarboxylic acid or a dicarboxylic acid. For purposes of the present invention the aromatic dicarboxylic acids or their reactive derivatives such as, for example, the acid halides, are preferred. Thus in these preferred aromatic dicarboxylic acids, as represented by Formula II, $R^2$ is a carboxyl group and $R^1$ is an aromatic radical such as phenylene, biphenylene, naphthylene, substituted phenylene, etc., two or more aromatic groups connected through non-aromatic linkages; or a divalent aliphatic aromatic radical. Some nonlimiting examples of suitable preferred aromatic dicarboxylic acids which may be used in preparing the the copolyestercarbonate resins of the instant invention include phthalic acid, isophthalic acid, terephthalic acid, homophthalic acid, o-, m-, and p-phenylenediacetic acid, the polynuclear aromatic acids such as diphenic acid, and 1,4-naphthalic acid. The aromatics may be substituted with Y groups in the same manner as the formula I aromatics are substituted.

These acids may be used individually or as mixtures of two or more different acids.

The carbonate precursor may be either a carbonyl halide, a carbonate ester, or a haloformate. The carbonyl halides which can be employed herein are carbonyl chlorides and carbonyl bromide. Typical of the carbonate esters which may be employed herein are diphenyl carbonate, di(halophenyl)carbonates such as di(chlorophenyl)carbonate, di(bromophenyl)carbonate, di(trichlorophenyl)carbonate, di(tribromophenyl)carbonate, etc., di(alkylphenyl)carbonates such as di(tolyl) carbonate, etc., di(naphthyl)carbonate, di(chloronaphthyl)carbonate, phenyltolyl carbonate, chloronaphthyl chlorophenyl carbonate, and the like. The haloformates suitable for use herein include bishaloformates of dihydric phenols such as bischloroformates of hydroquinone, etc. or glycols such as bis-haloformates of ethylene glycol, neopentyl glycol, polyethylene glycol, etc. While other carbonate precursors will occur to those skilled in the art, carbonyl chloride, also known as phosgene is preferred.

The preparation of copolyestercarbonates which may be employed in the compositions of the present invention is described in U.S Pat. Nos. 3,030,331; 3,169,121; 3,207,814; 4,194,038 and 4,156,069.

The copolyestercarbonates which are preferred in the practice of the present invention include the aromatic polyestercarbonates derived from dihydric phenols, aromatic dicarboxylic acids or their reactive ester forming derivatives such as the aromatic diacid halides, and phosgene. A particularly useful class of aromatic copolyestercarbonates is that derived from bisphenol-A, isophthalic acid, terephthalic acid, or a mixture of isophthalic acid and terephthalic acid, or the reactive derivatives of these acids such as terephthaloyl dichloride, isophthaloyl dichloride, or a mixture of isophthaloyl dichloride and terephthaloyl dichloride, and phosgene. The molar proportion of ester units in the copolyestercarbonate is generally from about 25 to 90 mole percent and preferably about 35 to 80 mole percent. The molar range of terephthalate units, the remainder of the copolymer ester units preferably comprising isophthalate units is generally from about 2 to 90 percent, and preferably from about 5 to about 25 percent.

The boron containing compounds useful in composition include boron compounds as enumerated previously wherein the R group is alkyl of from one to about twenty-four carbon atoms, inclusive, cycloalkyl of four to fourteen carbon atoms, inclusive, alkenyl of two to twenty-four carbon atoms, inclusive, aryl of six to fourteen carbon atoms, substituted aryl wherein the substituent is alkyl of one to six carbon atoms, halo or alkoxy of one to six carbon atoms. When the R is connected to a second oxygen group as in a biborate, the R becomes divalent, that is, for example, alkylene instead of alkyl, phenylene instead of phenyl, cycloalkylene instead of cycloalkyl, and the like, and is designated by R'. Examples of such boron compounds with an R group include $$B(OR)_3 \qquad \text{FIG. IV}$$

wherein the individual R is the same or different, $$R_1B(OR)_2 \qquad \text{FIG. V}$$

wherein the individual R is the same or different and $R_1$ is an aryl or an alkyl, preferably an aryl,

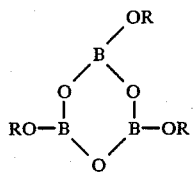

FIG. VI generally known as a boroxine wherein each R is the same or different.

The above organoboron compounds are prepared by methods known in the art, see Lappert in Chemical Reviews, 56, pp. 959–1064 (1956).

Also of significant interest and a preferred substructure are the biborates utilizing the divalent radial

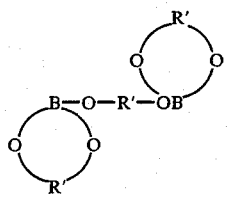

FIG. VII wherein R' is the same or different.

The biborates of Figure VII are prepared by methods known in the art, for example, see Kirk-Othmer Encyclopedia of Chemical Technology, 4, 3rd Ed. (1978) pg. 116. Various biborates are available commercially from U.S. Borax Research, for example the biborate of trihexylene glycol and of tri(butylene glycol) available as Borester 7 and Borester 35, respectively.

When using R', as in the biborates, the divalent radical is the same as R only a further hydrogen atom is missing, as aforementioned. Examples of such R' are alkylene instead of alkyl, cycloalkylene instead of cycloalkyl, alkenylene instead of alkenyl, arylene instead of aryl and the like.

When making a biborate of structure $B_2O_6R'_3$, hexylene glycol, the final structure including the six membered alkylene group is

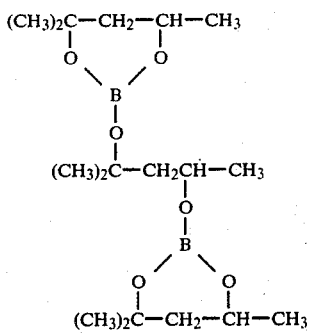

As used in the specification and claims, alkyl of one to twenty-four carbon atoms, inclusive, includes methyl, ethyl, propyl, isobutyl, pentyl, neopentyl, hexyl, 2,3-dimethylbutyl, 2,2,4-trimethyl octyl, decyl, isododecyl, lauryl, isoeicosyl and the like. Alkenyl of two to twenty-four carbon atoms, inclusive, include normal and branched alkenyl of the same type as mentioned for alkyl but containing one less hydrogen atom because of the presence of an unsaturate, a double bond, in the molecule. Cycloalkyl of four to fourteen carbon atoms, inclusive, include cyclobutyl, cycloheptyl, cyclononyl, cyclorindecyl, cyclomyristyl and the like. Aryl of 6–14 carbon atoms includes phenyl, biphenyl, naphthylyl and anthracenyl. Substituted aryl includes tolyl, o-xylyl, m-xylyl, p-xylyl, chlorobenzene, m-chlorotoluene, 1-butoxy naphthalene, n-hexocychlorobenzene, and the like. Halo is preferably chloro and bromo.

The admixtures of the aromatic carbonate polymer are simply prepared by standard techniques, for example dry mixing and melt extruding at an elevated temperature. The extruded admixture is then molded into a piece of specific dimensions or further extruded into a film or sheet product.

Various other additives may be employed in their appropriate quantities if they do not substantially detract from the final application. For example, the composition can be thermally stabilized by a phosphite, hydrolytically stabilized by an epoxide or flame retarded with a salt or brominated polymer.

The boron compounds can be effectively added to aromatic carbonate polymers blended with other polymers as well. Illustrative of these polymer types include acrylates, polyolefins, EDPM type polymers, styrenics, butadiene, amorphous copolyester and the like.

The amorphous copolyester is preferred and is prepared from 1,4-cyclohexanedimethanol and aromatic diacids or diacid ester, usually of the isophthalic acid family, the terephthalic acid family or mixtures of the isophthalic acid and terephthalic acid. Amorphous copolyesters with reaction residues of 1,4-cyclohexanedimethanol and a mixture of terephthalic and isophthalic acid are marketed under the trademark Kodar A150® by Eastman. The glycol portion of this type of copolymer need not only be made up of 1,4-cyclohexanedimethanol residues but may contain residues of other glycols, usually alkylene glycols having two to ten carbon atoms, preferably two to four carbon atoms, more preferably two carbon atoms, i.e. ethylene. Generally the molar ratio of the 1,4-cyclohexanedimethanol to ethylene glycol in the glycol portion is from about 4:1 to 1:4, with an acid portion comprising terephthalic acid, or isophthalic acid or mixtures of both acids.

The copolyester component may be prepared by procedures well known to those skilled in this art, such as by condensation reactions substantially as shown and described in U.S. Pat. No. 2,901,466.

The copolyesters for use in the subject invention generally will have an internal viscosity of at least about 0.4 dl/gm as measured in 60/40 phenol/tetrachloroethane or other similar solvent at about 25° C. and will have a heat distortion temperature of from about 60° C. to 70° C. The relative amounts of the 1,4-cyclohexanedimethanol to ethylene glycol in the glycol portion may vary so long as the molar ratio of 1,4-cyclohexanedimethanol to ethylene glycol is from 1:4 to 4:1.

A preferred copolyester for use as the amorphous polyester copolymer blend component in the subject invention is a copolyester as described above wherein the glycol portion has a predominance of ethylene glycol over 1,4- cyclohexanedimethanol, for example greater than 50/50 and especially preferably is about 70 molar ethylene glycol to 30 molar 1,4-cyclohexanedimethanol and the acid portion is terephthalic acid. A preferred copolyester of this type is commercially available under the tradename KODAR PETG 6763 from Eastman Chemical Company. A further preferred copolyester is where the 1,4-cyclohexanedimethanol is predominant molar wise over the ethylene glycol. A copolyester of this type is commercially available from Eastman Chemical under the tradename KODAR PCTG.

The radiation employed to achieve sterilization of the particular object is ionizing radiation, usually gamma radiation. The quantity of gamma radiation depends upon various factors such as thickness of the irradiated article and the like but is generally 0.5 to about 7 Megarads. Preferably, the irradiation is from about 1.0 to 3.0 Megarads.

The amount of boron compound necessary to achieve an anti-yellowing effect upon sterilization irradiation of the aromatic carbonate polymer admixture can vary widely. Generally from about 0.01 to about 2.0 weight percent of the boron compound is used as measured by the aromatic carbonate polymer. A more specific range is from about 0.2 to 1.5 weight percent. A preferred range is from about 0.3 to 1.0 weight percent. The exact quantity of a specific boron compound depends upon its specific activity and the nature of the aromatic carbonate polymer article in which it is admixed.

As stated previously, this method can be used to successfully inhibit irradiation yellowing of aromatic carbonate polymers in a variety of structures, for example, packaging containers for the irradiated medical materials and polycarbonate containing medical devices such as blood oxgenators, anesthesia canisters, blood centrifuge bowls and the like.

Below are examples of the invention. These examples are intended to illustrate rather than limit the broad concept of the invention. In all the examples below 1500 g of resin was employed in each sample, together with 0.9 g of a phosphite.

EXAMPLE I

Dry blends of bisphenol-A polycarbonate (LEXAN® 145, General Electric Company) and a conventional phosphite stabilizer were extruded with 3.5 g tri-n-amylborate (Sample 2) and without borate (Sample 1) at a 500° F. on a Sterling single screw extruder. One-eighth inch stepchips were molded using a 570° F. melt set temperature, 180° F. mold set temperature, and a 10/20 cycle time on a 3 oz. Van Dorn.

The samples were irradiated at 4 doses with a $Co^{60}$ source in a continuous conveyor system. The dosimetry was monitored with a calibrated NBS, radiochromic nylon dosimeter. The yellowness index (YI) of the samples a prior to and after irradiation was measured according to ASTM D1925 on a Gardner XL23 Colorimeter and the results are reported below.

| SAMPLE | 1 | 2 |
|---|---|---|
| YI  0 Mrad | 2.4 | 2.0 |
| YI 1.5 Mrad | 9.7 | 8.6 |
| YI 2.7 Mrad | 16.7 | 11.9 |
| YI 3.0 Mrad | 16.5 | 13.1 |
| YI 5.8 Mrad | 31.5 | 25.2 |

EXAMPLE II

Dry blends of bisphenol-A polycarbonate (LEXAN® 145, General Electric Company), a phosphite stabilizer, and the specified borates were extruded at 500° F. on a Sterling single screw extruder. One-eighth inch stepchips were molded using a 570° F. melt set temperature, 180° F. mold set temperature, and a 10/20 cycle time on a 3 oz. Van Dorn. The borates employed in the compositions are described below.

| SAMPLE NO. | CONTROL 3 | 4 | 5 | 6 | 7 | 8 | 9 | 10 |
|---|---|---|---|---|---|---|---|---|
| LEXAN ®145 phosphite | zero borate | | | | | | | |
| tri-n-octylborate | | 5.1 g | | | | | | |
| tri-m,p-cresyl borate | | | 4.3 g | | | | | |
| triethanolamine borate | | | | 2.0 g | | | | |
| tri(hexylene glycol) biborate | | | | | 4.7 g | 7.4 g | | |
| tri(butylene glycol) biborate | | | | | | | 3.7 g | |
| hexylene glycol | | | | | | | | 3.5 g |

-continued

| SAMPLE NO. | CONTROL 3 | 4 | 5 | 6 | 7 | 8 | 9 | 10 |
|---|---|---|---|---|---|---|---|---|
| boric anhydride | | | | | | | | |

The samples were irradiated at 3 doses with a $Co^{60}$ source in a continuous conveyor system. The dosimetry was monitored with a calibrated NBS, radiochromic nylon dosimeter. The yellowness index of the samples prior to and after irradiation was measured according to ASTM D1925 on a Gardner XL 835 Colorimeter and the results are reported below.

| SAMPLE NO. | CONTROL 3 | 4 | 5 | 6 | 7 | 8 | 9 | 10 |
|---|---|---|---|---|---|---|---|---|
| YI 0 Mrad | 2.0 | 1.7 | 2.0 | 2.9 | 1.7 | 1.7 | 1.9 | 2.0 |
| YI 2.0 Mrad | 11.0 | 10.1 | 11.3 | 10.9 | 7.9 | 7.4 | 9.6 | 10.2 |
| YI 2.7 Mrad | 15.7 | 14.4 | 14.9 | 14.9 | 9.4 | 8.9 | 13.0 | 14.3 |
| Yi 5.5 Mrad | 32.7 | 27.9 | 25.2 | 24.5 | 18.8 | 17.4 | 23.1 | 26.8 |

EXAMPLE III

Dry blends of polycarbonate (LEXAN ® 145, General Electric Company), a conventional phosphite stabilizer and tri(hexylene glycol)biborate were extruded at 500° F. on a Sterling single screw extruder. One-eighth inch stepchips were molded using a 570° F. melt set temperature, a 180° F. mold set temperature, and a 10/20 cycle time on a 3 oz. Van Dorn. The borate content used in the compositions is described below

| SAMPLE NO. | CONTROL 11 | 12 | 13 | 14 |
|---|---|---|---|---|
| tri(hexylene glycol)biborate | | 1.3 g | 3.0 g | 4.7 g |

The samples were irradiated with 5.5 Mrad using a $Co^{60}$ source in a continuous conveyor system. The dosimetry was monitored with a calibrated NBS, radiochromic nylon dosimeter. The yellowness index of the samples prior to and after irradiation was measured according to ASTM 1925 on a Gardner XL835 Colorimeter and the results are reported below.

| SAMPLE NO. | CONTROL 11 | 12 | 13 | 14 |
|---|---|---|---|---|
| YI 0 Mrad | 1.9 | 2.0 | 2.0 | 1.6 |
| YI 5.5 Mrad | 42.5 | 34.0 | 35.3 | 29.6 |

EXAMPLE IV

Dry blends of a copolyester carbonate with 75% ester content, the ester content being about 93 mole % isophthalate and 7% terephthalate, and a conventional phosphite stabilizer were extruded with and without tri(hexylene glycol) biborate at 570° F. on a Sterling single screw extruder. One-eighth inch stepchips were molded using a 650° F. melt set temperature, a 240° F. mold set temperature and a 10/20 cycle time on a 3 oz. Van Dorn. The borate content of the compositions is described below.

| SAMPLE NO. | CONTROL 15 | 16 |
|---|---|---|
| tri(hexylene glycol)biborate | | 4.7 g |

The samples were irradiated with 5.4 Mrads using a $Co^{60}$ source in a continuous conveyor system. The dosimetry was monitored with a calibrated NBS, radio chromic nylon dosimeter. The yellowness index of the samples prior to and after irradiation was measured according to ASTM D1925 on a Gardner XL835 Colorimeter and the results are reported below.

| SAMPLE NO. | CONTROL 15 | 16 |
|---|---|---|
| YI 0 Mrad | 10.1 | 10.6 |
| YI 5.4 Mrad | 25.4 | 21.0 |

EXAMPLE IV

Dry blends of polycaroonare (LEXAN ® 145, General Electric Company), 80 weight percent, and poly(1,4-cyclohexanedimethanol-terephthalate-co-isophthalate) (KODAR A150, Eastman Kodak Company), 20 weight percent, were extruded along with conventional stabilizers and with and without tri(hexylene glycol) biborate at 540° F. on Sterling single screw extruder. One-eighth inch stepchips were molded using a 540° F. melt set temperature, a 150° F. mold set temperature and a 10/20 cycle time on a 3 oz. Van Dorn. The compositions are described below.

| SAMPLE NO. | 17 | CONTROL 18 |
|---|---|---|
| 70% phosphorous acid | 0.9 g | 0.9 g |
| tri(hexylene glycol) biborate | 4.7 g | |

The samples were irradiated at 2 doses with a $Co^{60}$ source in continuous conveyor system. The dosimetry was monitored with a calibrated NBS, radiochromic nylon dosimeter. The yellowness index of the samples prior to and after irradiation was measured according to ASTM D1925 on a Gardner XL835 Colorimeter and the results are reported below.

| SAMPLE NO. | 17 | 18 |
|---|---|---|
| YI 0 Mrad | 2.7 | 2.3 |
| YI 3.0 Mrad | 8.1 | 13.7 |
| YI 5.5 Mrad | 11.5 | 22.1 |

As can be observed from the results of all the above four experiments, the composition having the boron compound has a significantly lower change in Y.I. value after irradiation capable of sterilizing than the control sample not having the boron compound.

What is claimed is:

1. A composition sufficiently irradiated to achieve sterilization comprising an aromatic carbonate polymer in admixture with an anti-yellowing upon exposure to sterilization irradiation effective amount of a boron compound having as part of its structure at least one

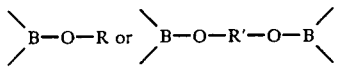

group wherein R is selected from alkyl of one to twenty-four carbon atoms, inclusive, alkenyl of two to twenty-four carbon atoms, inclusive, cycloalkyl of four to fourteen carbon atoms, inclusive, aryl of six to fourteen carbon atoms, inclusive; and substituted phenyl wherein there are one to three substituents which are the same or different and are alkyl of one to six carbon atoms, inclusive, alkoxy of one to six carbon atoms, inclusive, and halo; and R' is selected from the same group as R with a further hydrogen atom replaced by a bond to the second oxygen.

2. The composition in accordance with claim 1 wherein the boron compound is of the family B(OR)$_3$.

3. The composition in accordance with claim 1 wherein the boron compound is of the family R$_1$B(OR)$_2$ wherein R$_1$ is phenyl or an alkyl of one to twenty-four carbon atoms, inclusive.

4. The composition in accordance with claim 1 wherein the boron compound is

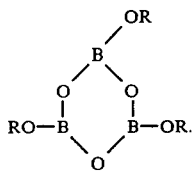

5. The composition in accordance with claim 1 wherein the boron compound is of the biborate family

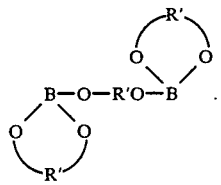

6. The composition in accordance with claim 2 wherein the aromatic carbonate polymer is polycarbonate.

7. The composition in accordance with claim 3 wherein the aromatic carbonate polymer is polycarbonate.

8. The composition in accordance with claim 4 wherein the aromatic carbonate polymer is polycarbonate.

9. The composition in accordance with claim 5 wherein the aromatic carbonate polymer is polycarbonate.

10. The composition in accordance with claim 2 wherein the boron compound is present in from about 0.01 to 2.0 weight percent of the aromatic carbonate polymer.

11. The composition in accordance with claim 3 wherein the boron compound is present in from about 0.01 to 2.0 weight percent of the aromatic carbonate polymer.

12. The composition in accordance with claim 4 wherein the boron compound is present in from about 0.01 to 2.0 weight percent of the aromatic carbonate polymer.

13. The composition in accordance with claim 5 wherein the boron compound is present in from about 0.01 to 2.0 weight percent of the aromatic carbonate polymer.

14. A method for inhibiting yellowing of irradiation sterilized aromatic carbonate polymer which comprises irradiation sterilizing a composition comprising an aromatic carbonate polymer and an anti-yellowing upon exposure to sterilization radiation effective amount of a boron compound having as part of its structure at least one

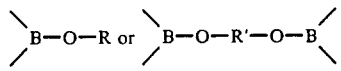

group wherein R is selected from alkyl of one to twenty-four carbon atoms, inclusive; alkenyl of two to twenty-four carbon atoms, inclusive; cycloalkyl of four to fourteen carbon atoms, inclusive; aryl of six to fourteen carbon atoms, inclusive; and substituted phenyl wherein there are one to three substituents which are the same or different and are alkyl of one to six carbon atoms, inclusive, alkoxy of one to six carbon atoms, inclusive, and halo; and R' is selected from the same group as R with a further hydrogen atom replaced by a bond to the second oxygen.

15. The method in accordance with claim 14 wherein the boron compound is of the family B(OR)$_3$.

16. The method in accordance with claim 14 wherein the boron compound is of the family R$_1$B(OR)$_2$ wherein R$_1$ is phenyl or an alkyl of one to twenty-four carbon atoms, inclusive.

17. The method in accordance with claim 14 wherein the boron compound is

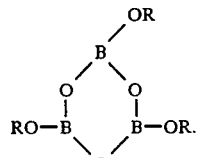

18. The method in accordance with claim 14 wherein the boron compound is of the biborate family

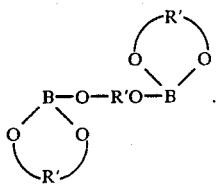

19. The method in accordance with claim 15 wherein the aromatic carbonate polymer is polycarbonate.
20. The method in accordance with claim 16 wherein the aromatic carbonate polymer is polycarbonate.
21. The method in accordance with claim 17 wherein the aromatic carbonate polymer is polycarbonate.
22. The method in accordance with claim 18 wherein the aromatic carbonate polymer is polycarbonate.
23. The method in accordance with claim 15 wherein the boron compound is present in from about 0.01 to 2.0 weight percent of the aromatic carbonate polymer.
24. The method in accordance with claim 16 wherein the boron compound is present in from about 0.01 to 2.0 weight percent of the aromatic carbonate polymer.
25. The method in accordance with claim 17 wherein the boron compound is present in from about 0.01 to 2.0 weight percent of the aromatic carbonate polymer.
26. The method in accordance with claim 18 wherein the boron compound is present in from about 0.01 to 2.0 weight percent of the aromatic carbonate polymer.
27. A composition comprising an aromatic carbonate polymer in admixture with an anti-yellowing upon exposure to sterilization irradiation effective amount of a boron compound of the family

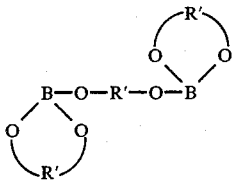

wherein R' is defined in claim 1.
28. The composition in accordance with claim 27 wherein R' is alkylene of two to about ten carbon atoms, inclusive.
29. The composition in accordance with claim 28 wherein R' is hexylene.
30. The composition in accordance with claim 2 wherein R is alkyl of one to about ten carbon atoms, inclusive.
31. The composition in accordance with claim 2 R is alkyl of three to about eight carbon atoms, inclusive.
32. The composition in accordance with claim 31 wherein R is n-amyl.
33. The composition in accordance with claim 31 wherein R is octyl.
34. The composition in accordance with claim 1 wherein a further resin is an admixture with the aromatic carbonate polymer.
35. The composition in accordance with claim 34 wherein the further resin is an copolyester derived from a glycol comprising 1,4-cyclohexanedimethanol and an acid portion of isophthalate, terephthalate or mixtures of the two.
36. The composition in accordance with claim 35 wherein the glycol portion also has alkylene glycol units of from two to ten carbon atoms, inclusive.
37. The composition in accordance with claim 36 wherein the alkylene glycol is ethylene glycol.
38. The composition in accordance with claim 37 wherein the molar ratio of ethylene glycol to 1,4cyclohexanedimethanol is from about 1:4 to 4:1.
39. The composition in accordance with claim 1 wherein the aromatic carbonate polymer is a copolyestercarbonate.
40. The composition in accordance with claim 39 wherein the copolyestercarbonate is derived from bisphenol-A.
41. The composition in accordance with claim 40 wherein the acid portion of the copolyestercarbonate is isophthalate, terephthalate or mixtures of the two.
42. The composition in accordance with claim 41 wherein the ester content is from about 25 to 90 mole percent.

* * * * *